United States Patent
Alas

(10) Patent No.: US 6,639,112 B1
(45) Date of Patent: Oct. 28, 2003

(54) METHOD FOR PREPARING KETONES BY PYROGENIC REACTION OF ALDEHYDES, ALCOHOLS, ACIDS OR ESTERS

(75) Inventor: Michel Alas, Melle (FR)

(73) Assignee: Rhodia Chimie, Bologne Billancourt Cedex (FR)

( * ) Notice: Subject to any disclaimer, the term of this patent is extended or adjusted under 35 U.S.C. 154(b) by 0 days.

(21) Appl. No.: 10/110,434

(22) PCT Filed: Oct. 20, 2000

(86) PCT No.: PCT/FR00/02934

§ 371 (c)(1),
(2), (4) Date: Apr. 12, 2002

(87) PCT Pub. No.: WO01/28967

PCT Pub. Date: Apr. 26, 2001

(30) Foreign Application Priority Data

Oct. 20, 1999 (FR) .............................................. 99 13093

(51) Int. Cl.[7] .......................... C07C 45/51; C07C 45/54
(52) U.S. Cl. ....................... 568/314; 568/318; 568/346; 568/350; 568/388; 568/391; 568/403; 568/458; 568/465
(58) Field of Search ................................. 568/314, 318, 568/346, 350, 388, 391, 403, 458, 465

(56) References Cited

U.S. PATENT DOCUMENTS 4,562,296 A   12/1985   Hargis

FOREIGN PATENT DOCUMENTS

GB        615 543 A       1/1949
GB       1 417 220       12/1975

OTHER PUBLICATIONS

Chemical Abstracts, vol. 106, No. 8, (Feb. 23, 1987), Abstract No. 052127.
Matsuoka et al., "Ketones", XP002141745 & JP 61 207354 A (Sep. 13, 1986).
Erwin Mueller–Erlwein, Chemical Ing. Tech., vol. 62, No. 5, pp. 416–417.

Primary Examiner—Samuel Barts
Assistant Examiner—Sikarl A. Witherspoon
(74) Attorney, Agent, or Firm—Burns, Doane, Swecker & Mathis, L.L.P.

(57) ABSTRACT

The invention concerns a method for preparing ketones of formula (I) wherein A and B are as defined in claim 1, consisting of reacting at a temperature ranging between 250 and 500° C. a compound of formula (II): A—X with a compound of formula (III): B—Y, wherein A, B, X and Y are as defined in claim 1, in a coolant solvent having a boiling point higher than 250 ° C., in the presence of a catalyst comprising at least a chemical compound of an element selected among alkali, alkaline-earth metals, lanthanides, Si, Al, Zn, Cu, Co, Fe, Mo, Mn, Cr, V, T, Zr, U, Rh, Tl, Ag, Cd, Pb, Y, Sc and Th, wherein the element is in divalent state or has a higher valency (I)

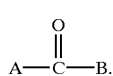

17 Claims, No Drawings

METHOD FOR PREPARING KETONES BY PYROGENIC REACTION OF ALDEHYDES, ALCOHOLS, ACIDS OR ESTERS

The invention relates to an improved catalytic process for preparing ketones by pyrogenation starting from the corresponding acids, alcohols, aldehydes or esters, employing temperatures of between 250 and 500° C. According to this process the pyrogenation reaction is conducted in liquid phase.

The production of ketones from the corresponding acids by pyrogenation has been widely described in the literature. The general process consists in contacting the acids in vapor phase with a catalyst maintained at a high temperature of between 300 and 550° C. depending on the nature of the reactants.

For a detailed description of this process, refer to Bull. Soc. Chim. 1909, 4(5), C.R. 1913, p. 220 and Bull. Soc. Chim. 1909, 4(5), No. 172.

The prior art's recommended catalyst is a metal oxide. A detailed review of the respective merits of the various metal oxides is given in Brennst. Chem. 1967, 48(3), 69–73.

As an appropriate catalyst mention may be made of thorium oxide, calcium oxide, iron oxide ($Fe_2O_3$), uranium oxide, manganous oxide (MnO), zirconium, manganese dioxide deposited on alumina, titanium oxide and the oxides of rare earths (oxides of the metals ranging from lanthanum (of atomic number 57) to lutetium (of atomic number 71), including scandium and yttrium) such as $CeO_2$, $La_2O_3$ or $Nd_2O_3$ deposited on gamma alumina.

The preparation of dialkyl ketones by pyrogenation of esters has also been described (cf. JP 48 076 806, 1972). There again, vapors of the ester are contacted with the catalyst (a zirconium) maintained at 400° C.

The same type of pyrogenation reaction, starting from aldehydes, was studied by the company Eastman Kodak. The process described in FR 1 533 651 employs the pyrogenation of vapors of aldehyde in contact with a catalyst maintained at 500° C., based on cerium oxide on alumina.

Alcohols may likewise be used as the starting product of the pyrogenation reaction for the purpose of preparing dialkyl ketones. JP 48 076 808, 1972, relates accordingly to a process which comprises contacting vapors of alcohol with a catalyst of the metal oxide type maintained at 420° C.

Generally speaking, the pyrogenation processes proposed hitherto in the art recommend contacting the reactants (acids, aldehydes, alcohols or esters) in vapor phase with the catalyst. The disadvantage associated with this type of process is the unavoidable formation of heavy impurities which gradually poison the catalyst.

In effect, the heavy impurities formed are deposited on the catalyst as they are formed and reduce its activity.

Regeneration of the catalyst requires prolonged shutdown of the reactors, without taking into account the fact that it does not allow the initial activity level to be attained and that it does not obviate replacement of the catalyst after a certain number of regeneration phases.

The process of the invention is aimed in particular at solving the problem of poisoning of the catalyst.

Surprisingly, the present inventors have shown that by conducting the reaction in liquid phase, in an appropriate solvent, i.e., by contacting the reactants with the catalyst in this solvent, it is possible to prevent poisoning of the catalyst.

Another advantage of the process of the invention is that it allows the use of a wide spectrum of catalysts. The success of the pyrogenation reaction is not dependent on the choice of metal oxides as catalyst. It is possible, for example, to operate in the presence of a variety of metal salts.

On the other hand, unlike the processes described in the prior art, the process of the invention does not require the employment of a catalyst which meets specific requirements in relation to particle size and specific surface.

Yet another advantage of the process of the invention is the possibility of operating at temperatures which generally are lower as compared with the temperatures required by the prior art processes.

The invention relates more specifically to a process for preparing ketones of formula I

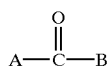

I in which:

A and B, which are identical or different, represent an optionally substituted saturated aliphatic hydrocarbon group; an optionally substituted aromatic hydrocarbon group; or an optionally substituted saturated carbocyclic group;

said process comprising reacting, at a temperature between 250 and 500° C., a compound of formula II:

II with a compound of formula III:

III in which:

A and B are as defined above; and X and Y, which are identical or different, represent a hydroxyl function, a carboxyl function, a —COH function or an ester function, in a heat carrier solvent having a boiling point of more than 250° C., in the presence of a catalyst comprising at least one compound of an element selected from alkali metals, alkaline earth metals, lanthanides, Si, Al, Zn, Cu, Ni, Co, Fe, Mo, Mn, Cr, V, Ti, Zr, U, Rh, Tl, Ag, Cd, Pb, Y, Sc and Th, in which the element is in the divalent state or has a higher valence.

A saturated aliphatic hydrocarbon group is a linear or branched saturated hydrocarbon group containing preferably from 1 to 40 carbon atoms or better still from 1 to 22 carbon atoms.

An aromatic hydrocarbon group is a carbocyclic aromatic group containing from 2 to 20 carbon atoms and consisting of an aromatic nucleus (monocyclic aromatic group) and/or of two or more aromatic nuclei which are fused or attached in pairs by σ bonds, the resulting structure forming either a star structure or a linear structure.

A saturated carbocyclic group is a cyclic, monocyclic or polycyclic hydrocarbon group containing preferably from 2 to 20 carbon atoms. According to the invention, the polycyclic radicals consist of rings fused with one another or attached in pairs by σ bonds, the resulting structure forming either a star structure or a linear structure.

The substituents carried by the saturated aliphatic hydrocarbon groups, the aromatic hydrocarbon groups and the saturated carbocyclic groups are those which are compatible with the pyrogenation reaction, i.e., those which do not give rise to secondary reactions.

According to one particularly preferred embodiment of the invention, A and B, which are identical or different, represent alkyl optionally substituted by one or more alkoxy, aryl or cycloalkyl radicals; aryl optionally substituted by one or more alkoxy, alkyl or cycloalkyl radicals; or cycloalkyl optionally substituted by one or more alkyl, alkoxy or aryl radicals.

An alkyl is a linear or branched aliphatic hydrocarbon chain containing preferably from 1 to 20 carbon atoms, better still from 1 to 10 carbon atoms, for example from 1 to 6 carbon atoms.

One preferred example of a substituted alkyl radical is an arylalkyl radical.

In the alkoxy radical, the alkyl part is as defined above.

An aryl is an aromatic hydrocarbon radical which is monocyclic or optionally consists of two or more fused aromatic nuclei, preferably $C_6$–$C_{18}$, for example $C_6$–$C_{10}$, such as phenyl, naphthyl, phenanthryl and anthryl.

The cycloalkyl radicals are monocyclic or polycyclic carbocyclic radicals (and especially monocyclic or bicyclic radicals) containing preferably from 3 to 10 carbon atoms, better still from 3 to 8 carbon atoms.

The term "polycyclic cycloalkyl" is intended to denote radicals comprising monocyclic nuclei fused with one another and/or monocyclic nuclei attached in pairs by σ bonds. Mention may be made for example of cyclopropyl, cyclobutyl, cyclopentyl, cyclohexyl, cycloheptyl, cyclooctanyl, adamantyl or norbornanyl.

An ester function is a functional group —CO—OR' in which R' represents a saturated or aromatic hydrocarbon radical, or else a radical containing both a saturated part and an aromatic part.

By way of example, R' represents alkyl optionally substituted by one or more alkoxy, aryl or cycloalkyl radicals; aryl optionally substituted by one or more alkoxy, alkyl or cycloalkyl radicals; or cycloalkyl optionally substituted by one or more alkyl, alkoxy or aryl radicals. More particularly it is preferred for R' to represent alkyl.

The asymmetric ketones of formula I in which A and B are different are prepared from the corresponding compounds of formula A—X and B—Y in which A and B are distinct from one another.

The preparation of the asymmetric ketones leads to the simultaneous formation of symmetric ketones A—CO—A and B—CO—B.

According to one preferred embodiment of the invention, the process of the invention is aimed at preparing the symmetric ketones of formula I in which A and B are identical. According to the process of the invention, the symmetric ketones are prepared starting from the compounds of formulae II and III in which A and B are identical.

Although the process of the invention can be employed starting from compounds II and III having distinct functional groups X and Y, it is particularly advantageous to employ the same type of reactants, i.e., reactants which have the same type of functionalization and for which X and Y are therefore identical.

Accordingly, the process of the invention is particularly appropriate for preparing ketones of formula $I_{sym}$:

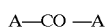

by pyrogenating a compound of formula II:

In this case, the compounds II and III are identical (A=B and X=Y) and the reaction takes place starting from one and the same compound.

For implementing the process of the invention it; is also preferable for X and Y respectively to represent —COOH:

in this case, the compounds of formula II and III respectively are carboxylic acids.

When X and/or Y represents —COOH, the selectivity is generally better, the yields are generally better, and a longer catalyst life is generally observed.

The preferred carboxylic acids (as compounds of formula II and III) are those which possess, α to the carboxyl function, a carbon atom which carries at least one hydrogen atom.

Examples of acids which can be used in accordance with the invention are the following:

saturated aliphatic monocarboxylic acids such as formic, acetic, propionic, butyric, isobutyric, valeric, isovaleric, pivalic, lauric, myristic, palmitic and stearic acid;

aromatic monocarboxylic acids such as benzoic acid, naphthalenecarboxylic acids and toluic acids;

arylaliphatic monocarboxylic acids in which the aliphatic part is saturated and the aryl part is optionally substituted, such as, in particular, arylpropionics such as 2-phenylpropionic acid, 2-[4-(but-2-yl)phenyl] propionic acid, 2-(3-benzoyl-phenyl)propionic acid, 2-(6-methoxynapth-2-yl)pro-pionic acid.

The heat carrier solvent as defined in the invention is a solvent which is capable of solubilizing each of the reactants of formulae II and III and which has a boiling point of more than 250° C.

More specifically, the solvent must have a boiling point which is higher than the chosen pyrogenation reaction temperature.

It should be understood that, in accordance with the invention, the solvent may be solid at ambient temperature provided it is in the liquid state at the reaction temperature.

Examples of solvents are aliphatic solvents having long chains of paraffinic type.

Other examples of appropriate solvents are heavy aromatic solvents, consisting either solely of aromatic nuclei, such as biphenyl (and more generally the polyphenyls) or such as triphenylbenzene (and more generally the polyphenylbenzenes), or include both aromatic nuclei and saturated aliphatic parts such as triphenylmethane (and more generally the saturated aliphatic hydrocarbons substituted by one or more phenyl nuclei) or benzenes substituted by one or more arylalkyl radicals such as benzyl radicals and optionally by one or more alkyl radicals. By way of example of arylalkyl-substituted benzenes mention may be made of benzylbenzene and dibenzylbenzenes, and especially 1,4-dibenzylbenzene. An example of an arylalkyl-substituted benzene additionally substituted by an alkyl group is dibenzyltoluene.

A polyphenyl according to the invention is a compound comprising at least three phenyl nuclei, in which the phenyl nuclei are linked in pairs by σ bonds. The structures formed by alignment of the phenyl groups are either star-shaped or linear.

Other appropriate solvents are ethers with a boiling point of more than 250° C., such as diphenyl ether (and more generally diaryl ethers), or such as poly(alkylene oxides) in which alkylene contains from 2 to 4 carbon atoms. Preferred examples of poly(alkylene oxide) are polyethylene glycols whose molecular mass ranges between 400 and 10,000.

Ketones having a boiling point of more than 250° C. can also be used as solvents in the process of the invention. The ketones which can be used have, for example, the formula $R_1$—CO—$R_2$, in which $R_1$ and $R_2$ are selected from $C_1$–$C_{26}$ alkyl optionally substituted by oxo; $C_6$–$C_{18}$ aryl optionally substituted by ($C_1$–$C_6$)alkoxy or ($C_1$–$C_6$)alkyl; and biphenyl, or else $R_1$—CO—$R_2$ forms a cyclic ketone in which CO forms part of a 5- to 8-membered ring optionally fused with one or more phenyl nuclei, said ring further being optionally substituted by one or more oxo, ($C_1$–$C_6$)alkyl or ($C_1$–$C_6$)alkoxy radicals.

By way of illustration mention may be made of anthraquinone, benzoylbiphenyls, methoxybenzophenones, distearyl ketone, dipalmityl ketone, dibenzoylmethane and stearylbenzoylmethane.

Alternatively, the tertiary amines of formula $R_aR_bR_cN$ in which $R_a$, $R_b$ and $R_c$ are selected independently from ($C_1$–$C_{22}$)alkyl (preferably ($C_8$–$C_{22}$)alkyl) optionally interrupted by one or more heteroatoms selected from O and S (preferably optionally interrupted by one or more oxygen atoms) can be used as solvents. By way of examples mention may be made of trioctylamine, trilaurylamine, tristearylamine ($N[(CH_2)_{17}$—$CH_3]_3$) and trisdioxaheptylamine.

According to one particularly preferred embodiment the heat carrier solvent is a saturated or unsaturated aliphatic carboxylic acid or else a metal salt of such an acid, such as an alkali metal salt, an alkaline earth metal salt or a transition metal salt.

Preferred examples of saturated and unsaturated aliphatic carboxylic acids are the $C_8$–$C_{24}$ acids, for example $C_{10}$–$C_{22}$ acids.

As saturated carboxylic acid mention may be made of capric, lauric, myristic, arachidic, behenic, lignoceric, hexacosanoic, pentadecanoic, heptadecanoic, heneicosanoic, tricosanoic, palmitic or stearic acids, preferably stearic and palmitic acids and mixtures thereof.

As unsaturated carboxylic acid mention may be made of linoleic, oleic, eicosenoic, nervonic, eicosadienoic, docosadienoic, myristolic, palmitoleic, arachidonic, vaccenic, eicosapentaenoic, docosapentaenoic, docosahexaenoic, elaidic and erucic acids.

Preferred examples of salts of carboxylic acids are the sodium, zinc and aluminum salts.

According to one particularly preferred embodiment of the invention, the solvent is selected from stearic acid, palmitic acid, zinc stearate, zinc ethylhexanoate or sodium palmitate.

Another type of heat carrier solvent which can be used according to the invention is the ketone of formula R°—CO—R°, R° being such that R°—COOH corresponds to the definition given above of the preferred heat carrier solvent of the saturated or unsaturated aliphatic carboxylic acid type.

By way of example of a ketone suitable as heat carrier solvent mention may be made of distearyl ketone.

More generally it is preferred for the heat carrier solvent to comprise one of the preferred heat carrier solvents having a boiling point of more than 250° C. that were defined above and to be selected from saturated or unsaturated aliphatic carboxylic acids; the metal salts of said carboxylic acids such as the alkali metal salts, alkaline earth metal salts or transition metal salts; the symmetric ketones derived from said carboxylic acids, of formula R°—CO—R° in which R° is such that R°—COOH represents a saturated or unsaturated aliphatic carboxylic acid as defined above; and mixtures thereof.

Furthermore, the heat carrier solvents of the heavy aromatic solvent type as defined above, or solvents comprising at least one such heavy aromatic solvent, are preferred.

When the solvent is a carboxylic acid or a ketone R°—CO°R°, the process of the invention is particularly appropriate for the preparation of ketones of formula I whose boiling point is less than 250° C.

Surprisingly, the formation in the reaction medium of the ketone resulting from the pyrogenation of the solvent of carboxylic acid type is not disruptive according to the invention.

More generally it is possible to use, as solvent, the heavy fractions obtained from the distillation of crude petroleum.

Another example of an aromatic hydrocarbon is the eutectic mixture of biphenyl and biphenyl oxide, which is referred to by the commercial designations THERMINOL VP1, DOWTHERM or GILOTHERM DO.

It is also possible to mention sulfolane and silicone oils having a temperature of more than 250° C.

Other examples are heavy aromatic hydrocarbons such as those sold by the companies MONSANTO and HULS under the brand names SANTOTHERM (mixture of triphenyl and tetraphenyl) and MARLOTHERM (dibenzyltoluene) respectively.

The heavy solvent according to the invention is one having a boiling point of more than 250° C.

The catalyst which can be used according to the invention comprises an active substance optionally deposited on an inert support. Appropriate inert supports include alumina, silica, synthetic or modified clays, and zeolites.

The form of the catalyst and its specific surface are not critical according to the invention. Accordingly, the catalyst may be present alternatively in the form of an extrudate, pellets, granules or a powder.

The active substance comprises at least one compound of an element selected from alkali metals, alkaline earth metals, lanthanides, Rh, U, Tl, Ag, Si, Al, Zn, Cu, Ni, Co, Fe, Mo, Mn, Cr, V, Ti, Zr, Cd, Pb, Y, Sc and Th, in which the element is in the divalent state or has a higher valence.

It should be understood that the catalysts generally used in the art for preparing ketones by pyrogenation of carboxylic acids, alcohols, esters and/or aldehydes can also be used in the context of the invention.

When the compounds II and III are carboxylic acids the active substance of the catalyst preferably comprises at least one compound of an element selected from alkali metals, alkaline earth metals, lanthanides, Si, Al, Zn, Cu, Ni, Co, Fe, Mo, Mn, Cr, V, Ti, Zr, Cd, Pb, Y, Sc and Th.

Among preferred alkali metals mention may be made of sodium.

Among preferred alkaline earth metals mention may be made of calcium, magnesium and barium.

As preferred examples of lanthanides mention may be made of Ce, Pr, Nd, Sm, Gd and Yb.

With particular advantage the catalyst comprises at least one chemical compound of an element selected from manganese, thorium, zirconium, calcium and iron. Even more preferably the catalyst comprises manganese, thorium or a mixture of these elements.

It should be understood in effect that the active substance may comprise more than two distinct chemical compounds, each compound being based on an identical or different element selected from the list of the abovementioned elements.

The exact nature of the chemical compounds forming the active substance is not critical according to the invention provided that the element it comprises, selected from the above list, is in the divalent state or has a higher valence.

Advantageously the element is divalent.

Said chemical compound may be an oxide of said element or a single or double, mineral or organic salt. Examples of mineral salts are nitrates, sulfates, oxysulfates, halides, oxyhalides, silicates, carbonates, orthophosphates, metaphosphates, hydrogen phosphates and pyrophosphates.

Examples of organic salts are acetylacetonates, alkoxides and, for example, methoxide and ethoxide, or $C_1$–$C_6$ carboxylates such as acetate or carboxylates derived from $C_8$–$C_{22}$ fatty acids and particularly stearate, palmitate, myristate and laurate.

As preferred salts mention may be made of acetates, carbonates and stearates.

More specifically, the following salts are appropriate as active substances for the catalysis of the process of the invention:

manganese acetate;
manganese nitrate;
manganese carbonate;
manganese stearate;
manganese laurate;
manganese myristate;
manganese caprate;
thorium acetate;
thorium nitrate;
thorium carbonate;
thorium stearate;
thorium laurate;
thorium myristate; and
thorium caprate.

As oxides it will be possible to use with advantage all those recommended in the literature for this type of reaction, and especially one or more of the following oxides: thoria, uranium oxides, calcium oxide, ferric oxide ($Fe_2O_3$), titanium oxide, zirconia, manganous oxide (MnO), manganese dioxide, cerium oxide, $La_2O_3$ and $Nd_2O_3$.

When the compounds of formulae II and III are carboxylic acids it is preferable for said catalyst to comprise at least one chemical compound of an element selected from Na, Ca, Mg, Ba, Si, Al, Zn, Cu, Mn, Ni, Co, Fe, Mo, Cr, V, Ti, Zr, Cd, Pb, Y, Sc, Th, Ce, La, Pr, Nd, Sm, Gd and Yb.

The active substance of the catalyst preferably comprises one or more compounds selected from manganese oxide, manganese carbonate, manganese acetate and manganese stearate.

In one particular embodiment of the invention the compounds forming the active substance are fixed to an inert support, such as silica, or a synthetic or modified clay, but more preferably alumina or a zeolite. The preparation of catalysts fixed to an inert support can be carried out in a conventional manner.

One known method for preparing metal oxides fixed to an inert support consists in dissolving a salt of the selected metal in water and in pouring the resulting solution onto particles of the activated inert support. The product is then calcined in order to ensure conversion of the metal salt to metal oxide fixed to the inert support.

The process of the invention consists in contacting the catalyst in a heat carrier solvent having a boiling point of more then 250° C. with the compounds II and III at a temperature of 250–500° C., preferably at a temperature of between 300 and 400° C.

According to the invention, said contacting can be carried out in any way whatsoever.

Preferably, however, a suspension of the catalyst in the heat carrier solvent is prepared and is brought to the desired temperature of between 250 and 500° C.

The suspension may be heated conventionally by a circuit of a thermal fluid, by a melted salt mixture or else directly by direct electrical heating by resistance or by induction.

In order to accelerate heat transfer it is advantageous to stir the suspension of the catalyst in the solvent throughout the reaction period.

Subsequently, the reactants (compounds of formulae II and III) are introduced into the reaction medium. The sequence of introduction and the time of introduction into the reaction medium are not critical according to the invention and will be readily adjustable by the person skilled in the art.

In general the ketone produced by the reaction exits the reactor in vapor form as a mixture with other reaction byproducts, such as for example water vapor and carbon dioxide. The recovery of the ketone involves cooling the vapors and condensing them.

In the case of ketones of formula I having a high boiling point it is desirable to add a certain amount of water to the condensed mixture recovered in order to carry out an azeotropic distillation.

The process of the invention may be carried out continuously or batchwise.

When it is carried out continuously, it may be advantageous to draw off some of the liquid phase from the reactor while compensating the loss of solvent by introducing a corresponding amount of solvent into the reaction medium.

This operation allows some of the heavy impurities formed during the reaction to be evacuated from the reactor.

It will be noted, however, that the presence of the heavy impurities which form during reaction does not have an adverse effect on the satisfactory progress of the reaction. On the contrary, an improvement in the overall yield of the reaction and in the productivity is generally observed.

Without wishing to be limited to any particular theory, it is thought that the presence of these impurities in the reaction medium has the effect of enhancing the overall heat transfer and hence the productivity. This capacity to enhance heat exchange can be attributed to the intrinsic properties of the impurities, namely their viscosity and thermal conductivity.

According to one preferred embodiment of the invention, the reaction will not be continued through to total conversion of the reactants.

It is preferably desirable to interrupt the reaction when from 50 to 80 mol % of the respective ketone have been obtained, irrespective of whether the process is carried out continuously or batchwise.

The degree of conversion of the reactants can be adjusted very simply by acting on the reaction temperature, the reactant feed rate or the amount of reactants introduced and the mass of catalyst in the reactor.

In this way, the vapors exiting the reactor contain not only the ketone but also a considerable quantity of reactants which are appropriately separated and then recycled to the reactor.

Separation can be carried out employing any technique whatsoever; for example, by fractional distillation, by liquid-liquid extraction or by crystallization.

The advantages of the process of the invention in relation to the prior art process are several:

the required reaction temperatures are lower;
the selection of catalysts which can be used is wider;
the yields and productivity are improved;
the poisoning of the catalyst is avoided.

The invention is illustrated below in the light of the following examples. In these examples, the process of the invention was implemented continuously.

EXAMPLE 1

A stirred reactor heated by a network of electrical resistors is charged with 600 g of MARLOTHERM S solvent and 150 g of manganese carbonate. The suspension is heated to reach 380° C. and 102 g/h of isobutyric acid are introduced continuously. The vapors exiting the reactor are cooled to 105/130° C. and then condensed at 5° C., thereby permanently producing a heterogeneous mixture having the following average composition: 78.9 g/h of an organic layer (analysis: 62.4% diisopropyl ketone and 32% isobutyric acid and 3.6% water) and 5 g/h of water containing virtually no diisopropyl ketone or isobutyric acid. The yield of diisopropyl ketone relative to the isobutyric acid consumed is 99%.

EXAMPLE 2

A stirred reactor heated by a network of electrical resistors is charged with 600 g of MARLOTHERM S solvent and 70 g of manganous oxide (MnO). The suspension is heated to reach 380° C. and 102 g/h of isobutyric acid are introduced continuously. The vapors exiting the reactor are cooled to 105/130° C. and then condensed thereby permanently producing a heterogeneous mixture containing 78.5 g/h of an organic layer having the same composition as in example 1.

EXAMPLE 3

The procedure of example 1 is repeated, lowering the temperature of the reactor to 360° C. and feeding it with 90 g/h of isobutyric acid. A heterogeneous mixture is recovered which contains 42 g/h of diisopropyl ketone and 19.3 g/h of isobutyric acid.

EXAMPLE 4

A stirred metal reactor heated by a magnetic induction system is charged with 550 g of distearyl ketone and 80 g of manganese oxide (MnO). The suspension is heated to reach 330° C., and 25 g/h of isobutyric acid are fed in. Permanently, a mixture is recovered which contains 12.6 g of isobutyric acid and 7.9 g of diisopropyl ketone. The level in the reactor remains perfectly stable after continuous operation for 100 h.

EXAMPLE 5

The same reactor as that in example 4 is charged with 600 g of a stearic/palmitic acid mixture (ratio: 80/20 by weight) and 70 g of manganese oxide (MnO). The suspension is heated to 330° C. and maintained at this temperature for 24 h. It is then fed with 25 g/h of isobutyric acid, heating to hold the temperature at 330/335° C. Permanently, a mixture is recovered which contains 12 g/h of isobutyric acid and 8 g/h of diisopropyl ketone.

EXAMPLE 6

The procedure of example 5 is repeated, replacing the 70 g of manganese oxide by 105 g of manganese carbonate. The results obtained are exactly the same.

EXAMPLE 7

The procedure of example 5 is repeated, replacing the 80/20 stearic/palmitic acid mixture by a 20/80 stearic/palmitic acid mixture. The results obtained are the same as for example 5.

What is claimed is:
1. A process for preparing ketones of formula I

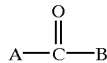

in which:
A and B, which are identical or different, are selected from the group consisting of an optionally substituted saturated aliphatic hydrocarbon group; an optionally substituted aromatic hydrocarbon group; and an optionally substituted saturated carbocyclic group;
said process comprising reacting, at a temperature between 250 and 500° C., a compound of formula II:

with a compound of formula III:

in which:
A and B are as defined above; and X and Y, which are identical or different, are selected from the group consisting of a hydroxyl function, a carboxyl function, a —COH function and an ester function,
in a heat carrier solvent having a boiling point of more than 250° C., in the presence of a catalyst comprising at least one chemical compound of an element selected from alkali metals, alkaline earth metals, lanthanides, Si, Al, Zn, Cu, Ni, Co, Fe, Mo, Mn, Cr, V, Ti, Zr, U, Rh, Tl, Ag, Cd, Pb, Y, Sc and Th, in which the element is in the divalent state or has a higher valence,
wherein the heat carrier solvent comprises a solvent having a boiling point of more than 250° C. which is selected from the group consisting of saturated or unsaturated aliphatic carboxylic acids; metal salts of said carboxylic acids; symmetric ketones derived from said carboxylic acids, of formula R°—CO—R° in which R° is such that R°—COOH represents a saturated or unsaturated aliphatic carboxylic acid; and mixtures thereof.

2. The process as claimed in claim 1, wherein A and B, which are identical or different, are selected from the group consisting of alkyl optionally substituted by one or more alkoxy, aryl or cycloalkyl radicals; aryl optionally substituted by one or more alkoxy, alkyl or cycloalkyl radicals; or cycloalkyl optionally substituted by one or more alkyl, alkoxy or aryl radicals.

3. The process as claimed in claim 1, wherein X and Y represent —COOH.

4. The process as claimed in claim 3, wherein the carbon of the radical A, attached directly to the group X in the compound II, and the carbon of the radical B, attached directly to the group Y in the compound III, carry at least one hydrogen atom.

5. The process as claimed in claim 1, wherein A and B are identical.

6. The process as claimed in claim 1, wherein alkyl contains from 1 to 20 carbon atoms, alkoxy contains from 1 to 20 carbon atoms, aryl contains from 6 to 18 carbon atoms and cycloalkyl contains from 3 to 8 carbon atoms.

7. The process as claimed in claim 1, wherein the reaction is conducted at a temperature of between 300 and 400° C.

8. The process as claimed in claim 1, wherein the reaction is conducted in a heat transfer solvent having a boiling point of more than 250° C. consisting of a solvent having a boiling point of more than 250° C. which is selected from the group consisting of saturated or unsaturated aliphatic carboxylic acids; the metal salts of said carboxylic acids; the symmetric ketones derived from said carboxylic acids, of formula R°—CO—R° in which R° is such that R° —COOH represents a saturated or unsaturated aliphatic carboxylic acid; and mixtures thereof.

9. The process as claimed in claim 1, wherein said chemical compound of the catalyst is in the form of an oxide or of a single or double, mineral or organic salt.

10. The process as claimed in claim 3, wherein the element of said chemical compound is selected from Na, Ca, Mg, Ba, Si, Al, Zn, Cu, Mn, Ni, Co, Fe, Mo, Cr, V, Ti, Zr, Cd, Pb, Y, Sc, Th, Ce, La, Pr, Nd, Sm, Gd and Yb.

11. The process as claimed in claim 1, wherein said compound of the catalyst is selected from manganese oxide, manganese carbonate, manganese acetate and manganese stearate.

12. The process as claimed in claim 1, wherein said compound of the catalyst is fixed to an inert support.

13. The process as claimed in claim 1, wherein the compounds of formulae II and III are introduced into a suspension of the catalyst in the heat carrier solvent maintained at 250–500° C.

14. The process as claimed in claim 13, wherein the ketone of formula I is recovered by separating the vapors escaping from the reaction medium.

15. The process as claimed in claim 12, wherein the inert support comprises alumina or a zeolite.

16. The process as claimed in claim 1, wherein the metal salts of said carboxylic acids comprise alkali metal salts, alkaline earth metal salts or transition metal salts.

17. The process as claimed in claim 8, wherein the metal salts of said carboxylic acids comprise alkali metal salts, alkaline earth metal salts or transition metal salts.

* * * * *